(12) United States Patent
Tamura et al.

(10) Patent No.: US 6,475,191 B2
(45) Date of Patent: Nov. 5, 2002

(54) INDWELLING NEEDLE ASSEMBLY

(75) Inventors: Kazuhiko Tamura; Hiroyuki Nakagami, both of Osaka (JP)

(73) Assignee: Nipro Corporation, Osaka (JP)

( * ) Notice: Subject to any disclaimer, the term of this patent is extended or adjusted under 35 U.S.C. 154(b) by 19 days.

(21) Appl. No.: 09/819,976

(22) Filed: Mar. 29, 2001

(65) Prior Publication Data

US 2001/0027292 A1 Oct. 4, 2001

(30) Foreign Application Priority Data

Apr. 4, 2000 (JP) ........................... 2000-101700

(51) Int. Cl.$^7$ ............................................. A61M 5/178
(52) U.S. Cl. .................... 604/164.08; 604/198
(58) Field of Search ................. 604/110, 162, 604/161, 164.01, 158, 165.01, 164.03, 171, 164.07, 198, 192, 195, 164.08

(56) References Cited

U.S. PATENT DOCUMENTS

| | | | | |
|---|---|---|---|---|
| 3,943,932 A | * | 3/1976 | Woo | 128/303.18 |
| 4,609,370 A | * | 9/1986 | Morrison | 604/165 |
| 5,000,740 A | | 3/1991 | Ducharme et al. | 604/162 |
| 5,356,387 A | | 10/1994 | Sirbola | 604/162 |
| 5,447,501 A | | 9/1995 | Karlsson et al. | 604/198 |
| 5,501,675 A | | 3/1996 | Erskine | 604/263 |
| 5,531,713 A | | 7/1996 | Mastronardi et al. | 604/263 |
| 5,584,812 A | * | 12/1996 | Martin | 604/164 |
| 5,676,658 A | * | 10/1997 | Erskine | 604/263 |
| 5,695,474 A | | 12/1997 | Daugherty | 604/162 |
| 5,769,827 A | * | 6/1998 | DeMichel et al. | 604/263 |
| 5,938,622 A | | 8/1999 | Chen | 600/576 |
| 6,001,080 A | * | 12/1999 | Kuracina et al. | |
| 6,221,047 B1 | * | 4/2001 | Greene et al. | 604/164 |
| 6,322,537 B1 | * | 11/2001 | Chang | 604/164.08 |

FOREIGN PATENT DOCUMENTS

| | | |
|---|---|---|
| EP | 0 448 395 | 3/1991 |
| EP | 0 576 302 | 6/1993 |
| EP | 0 763 369 | 9/1996 |
| JP | 11-057002 | 3/1999 |

OTHER PUBLICATIONS

Patent Abstract of Japan, Publication No. 03–063066, Publication Date Mar. 19, 1991.
Patent Abstract of Japan, Publication No. 06–078999, Publication Date Mar. 22, 1994.
Patent Abstract of Japan, Publication No. 06–086821, Publication Date Mar. 29, 1994.
Patent Abstract of Japan, Publication No. 08–215315, Publication Date Aug. 27, 1996.
Patent Abstract of Japan, Publication No. 09–103492, Publication Date Apr. 22, 1997.

* cited by examiner

*Primary Examiner*—Ira S. Lazarus
*Assistant Examiner*—Tu Cam Nguyen
(74) *Attorney, Agent, or Firm*—Kubovcik & Kubovcik

(57) ABSTRACT

An indwelling needle assembly includes an outer needle hub having an outer needle fixed to the distal end portion thereof, an inner needle hub having an inner needle at the distal end portion thereof, and a needle guard that can accommodate the inner needle and the inner needle hub therein. The needle guard has a double-tube structure including an inner tube and an outer tube, and a connector for connecting the inner needle hub and the inner tube via the proximal end of said needle guard. The needle guard is also expandable by sliding the outer tube toward the proximal end of the inner tube. When the needle guard is extended, the inner needle hub is slid in the needle guard toward the proximal end of the needle guard by the connector.

7 Claims, 12 Drawing Sheets

INDWELLING NEEDLE ASSEMBLY

TECHNICAL FIELD OF THE INVENTION

The present invention relates to an indwelling needle assembly including an indwelling needle to be detained temporarily in a blood vessel for an infusion or the like. More specifically, the present invention relates to an indwelling needle assembly in which after an inner needle and an outer needle are pierced simultaneously in a tissue of a living body and the inner needle is removed from the outer needle while retaining the outer needle, the inner needle can be stored within a needle guard safely and easily.

BACKGROUND OF THE INVENTION

An indwelling needle used for an infusion or the like generally has a double-needle structure comprising an outer needle and an inner needle inserted in a lumen of the outer needle, and when used, the assembly is pierced into a blood vessel with the inner needle. After the outer needle is inserted in the blood vessel to a prescribed position, the inner needle is removed from the lumen of the outer needle, and then an infusion line or the like is connected to a proximal end portion of the outer needle to allow an infusion, a liquid medicament or the like to flow into the blood vessel. Therefore, a soft resin product that has less possibility of damaging an inner wall of the blood vessel is used for the outer needle, and a metal product that can be easily pierced into the blood vessel is used for the inner needle.

After the outer needle is retained in a body of a patient, the removed inner needle is discarded. At this time, a member of a medical staff or a patient may be injured by inadvertently touching a sharp tip of the inner needle. Even when the tip of the needle is protected by a suitable means, an inner needle used for a patient suffering from a blood-borne disease such as acquired immune deficiency syndrome (AIDS) or hepatitis can be an infection vehicle that transmits these diseases not only through the tip but also through the needle itself.

Therefore, it is quite important to properly dispose of the inner needle that has been pierced into the patient. However, from a medical standpoint, treatment of the patient is given priority over the safety of the disposition of the inner needle in many cases.

In recent years, an indwelling needle assembly for discarding the used inner needle immediately and easily has been proposed (Japanese Patent Laid-Open No. 3-63066, Japanese Patent Laid-Open No. 6-78999, Japanese Patent Laid-Open No. 6-86821, Japanese Patent Laid-Open No. 11-57002).

Each of these indwelling needle assemblies comprises a tubular housing having an inner needle hub connected to the inner needle therein, and a needle guard slidably disposed between the housing and the inner needle hub and having a catheter connected to a distal end portion thereof, wherein after an outer needle of the indwelling needle assembly pierced into a patient is retained in the patient and the inner needle is removed, the inner needle is stored in the needle guard by sliding the needle guard toward the distal end of the housing. With these indwelling needle assemblies, when the inner needle is removed, the removed inner needle can easily be protected using one hand, and thus there is no risk of being injured by the tip of the inner needle or of being infected with disease by blood adhered to the inner needle.

However, since such an indwelling needle assembly is constructed to slide a needle guard that is longer than the inner needle toward the distal end of the housing by a length corresponding to the length of the inner needle, it is difficult for medical personnel who have small hands to slide the needle guard using one hand so as to completely protect the inner needle. In addition, in case of an emergent dialysis using a long indwelling needle to be retained in a femoral vein in an inguinal region, it is difficult even for medical personnel whose hands are not small to slide the needle guard using one hand to a position where the inner needle is completely protected.

On the other hand, in view of the problem described above, an indwelling needle assembly comprising a spring disposed between an inner needle hub and a proximal end portion of a needle guard has been developed (Japanese Patent Laid-Open No. 8-215315, Japanese Patent Laid-Open No. 9-103492). In the indwelling needle assembly, releasing a push-button locking mechanism allows the spring to urge the inner needle hub toward the proximal end of the needle guard.

However, in the indwelling needle assembly comprising such a push-button locking mechanism, it cannot be restored and thus the needle assembly may be put out of use in a case where a user releases the lock inadvertently by pushing the push-button.

In light of the circumstances described thus far, it is an object of the present invention to provide an indwelling needle assembly having such a structure that medical personnel can take the inner needle easily into the needle guard using one hand even when a long indwelling needle is used or even when it is used by a person who has small hands, and that cannot be put out of use by erroneous operation.

SUMMARY OF THE INVENTION

After an elaborate study to solve the problems described above, the present inventors found that the sliding distance of the needle guard required to store the inner needle can be reduced to about half that of the conventional indwelling needle assemblies by making the needle guard a double-tube structure including an inner tube and an outer tube, and providing a connector for connecting the inner tube and the inner needle hub in the needle guard via the proximal side of the outer tube, and thus the present invention is realized.

In other words, the present invention provides an indwelling needle assembly comprising an outer needle hub having an outer needle to be pierced into a tissue of a living body and retained therein fixed to the distal end portion of the hub, an inner needle hub having an inner needle being insertable into the lumen of the outer needle and having a sharp blade edge at the distal end fixed to the distal end portion of the hub, and a needle guard for accommodating the inner needle and the inner needle hub, characterized in that the needle guard has a double-tube structure including an inner tube and an outer tube, that the needle guard is provided with a connector for connecting the inner needle hub and the inner tube via the proximal side of the needle guard, in that the whole length of the needle guard can be extended by sliding the outer tube toward the proximal end of the inner tube, and in that as the whole length of the needle guard is extended, the inner needle hub is slid within the needle guard toward the proximal end of the needle guard by the connector.

DESCRIPTION OF THE DRAWINGS

Referring to the preferred embodiment and attached drawings, an indwelling needle assembly of the present invention will hereinafter be further described. However, the present invention is not limited thereto.

DETAILED DESCRIPTION OF THE INVENTION

Figure 1:
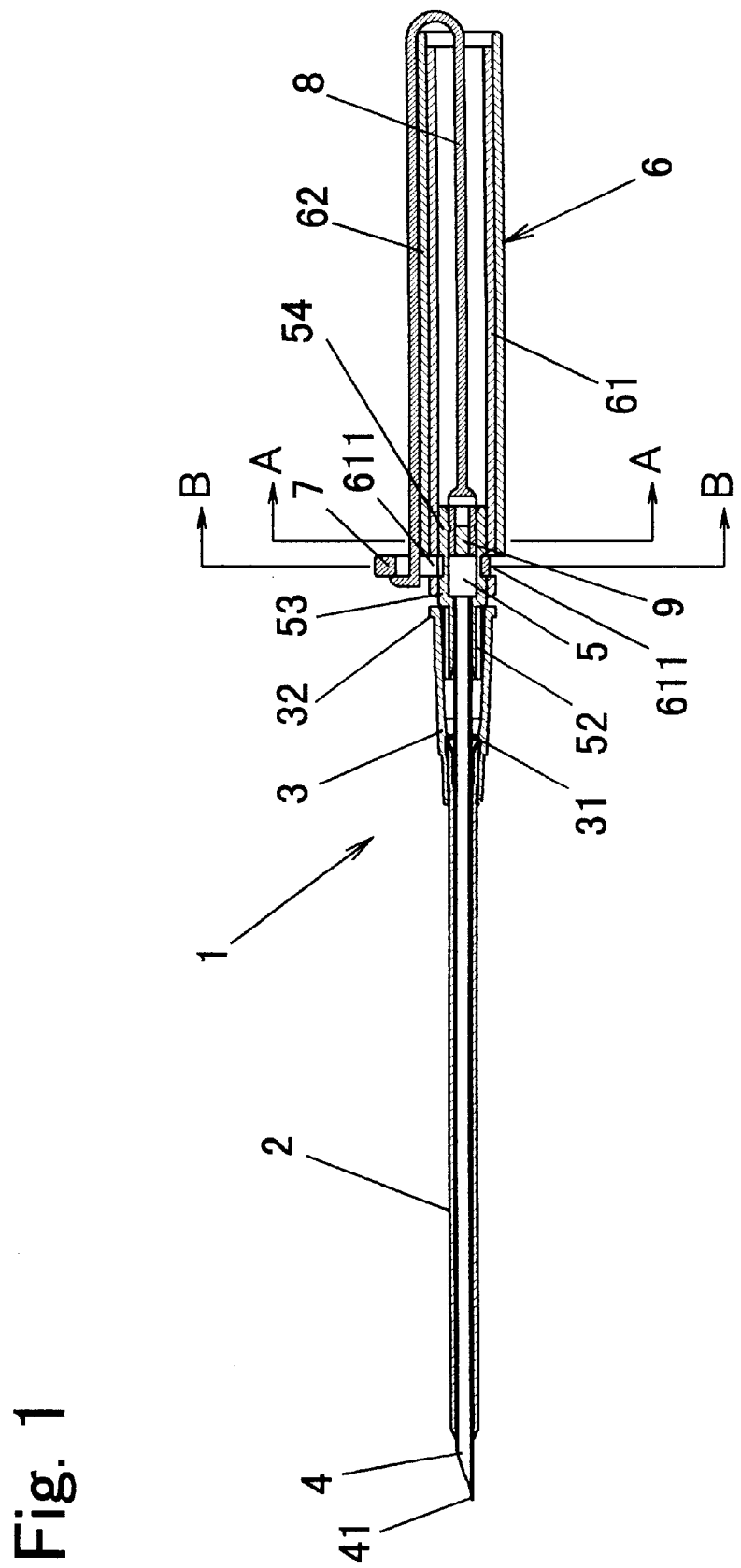
FIG. 1 is a cross sectional view of the indwelling needle assembly according to an embodiment of the present invention showing a state before the inner needle is protected as seen from the side.

As shown in FIG. 1, the indwelling needle assembly 1 of the present invention comprises an outer needle hub 3 having an outer needle 2 fixed to the distal end portion thereof, an inner needle hub 5 having an inner needle 4 which is insertable into the lumen of the outer needle 2 and having a sharp blade edge 41 at the distal end portion of the inner needle 4 and fixed to the distal end portion of the inner needle hub 5, and a needle guard 6 for accommodating the inner needle 4 and inner needle hub 5 therein.

In the indwelling needle assembly 1 of the present invention, the distal end designates the end which is to be pierced into the patient (left side in the figures), and the proximal end designates the end opposite the distal end (right side in the figures).

The outer needle 2 is a hollow tube, and the distal end portion is preferably formed in a tapered shape in which the outer diameter is gradually reduced toward the distal end so as to reduce the piercing resistance. The outer needle 2, which is inserted into a patient's body and retained for some time therein, is preferably formed of a soft resin that has less possibility of injuring the patient, and more specifically, is an ethylene-tetrafluoroethylene copolymer, a polyurethane, a polyether nylon resin, or the like.

The outer needle 2 may be broken for example when a patient moves while the outer needle 2 is retained in the patient's body. In order to detect a fragment of the outer needle 2 in such a case, it is also possible to add an X-ray contrast medium such as a barium sulfate or the like to the material for the outer needle 2 to provide a contrast medium function to the outer needle 2.

An outer needle hub 3 is fixed to the proximal end portion of the outer needle 2. As a method of fixing, caulking with a caulking pin 31, adhesion by means of an adhesive or fusion bonding by heat can be employed.

The outer needle hub 3 has a hollow tubular body and is formed in a tapered shape in which the inner diameter increases toward the proximal end. This shape ensures connection of a tube of an infusion set or the like. At the proximal end portion of the outer needle hub 3, there may be provided a projection 32 for connecting a luer tapered part of a locking type syringe or tube for an infusion set.

As a material for the outer needle hub 3, a hard resin such as polyethylene, polypropylene, polyolefin such as ethylene-vinyl acetate copolymer, polyvinyl chloride, polybutadiene, polyamide, polyester or the like is employed.

The inner needle 4 is a hollow tube insertable into the lumen of the outer needle 2, and the outside diameter thereof is slightly smaller than the inner diameter of the outer needle 2. The outer needle 2 is held by the inner needle 4 and thus there is no risk that the outer needle 2 will be detached unless a force is applied from the outside.

At the distal end portion of the inner needle 4, there is formed a sharp blade edge 41. The blade edge 41 has a bevel so as to reduce a piercing resistance. The inner needle 4 is pierced into the patient while being held in the outer needle 2, but it is required to have a length such that the blade edge 41 projects from the distal end of the outer needle 2 when the inner needle 4 is pierced into the patient.

As a material for the inner needle 4, a metal material such as stainless steel, aluminum, titanium, or an alloy of these metals is employed.

An inner needle hub 5 is fixed to the proximal end portion of the inner needle 4. As a method of fixing, adhesion by means of an adhesive or fusion bonding by heat can be employed similar to fixing of the outer needle 2 and the outer needle hub 3.

Figure 6:
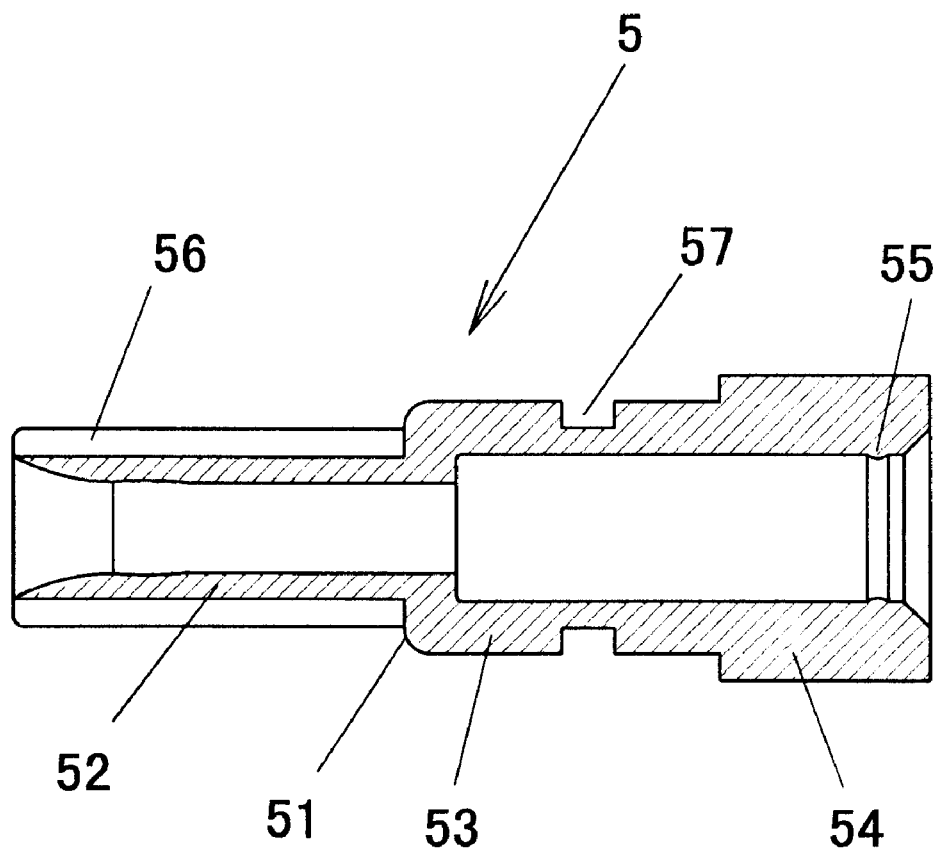
FIG. 6 is an enlarged cross sectional view of the inner needle hub of the indwelling needle assembly shown in FIG. 1 as seen from the top.
Figure 7A:
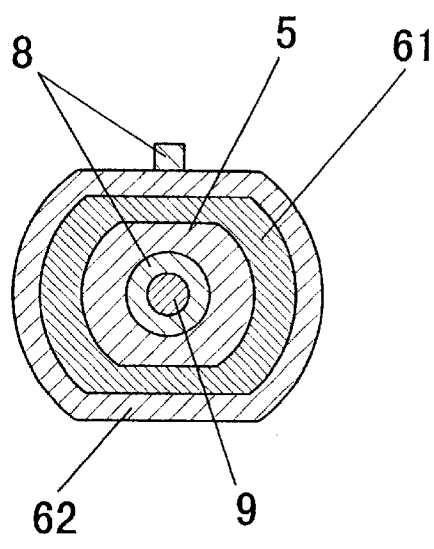
FIGS. 7(a) and 7(b) are alternative cross sectional views of the indwelling needle assembly shown in FIG. 1 taken along the line A—A.
Figure 8:
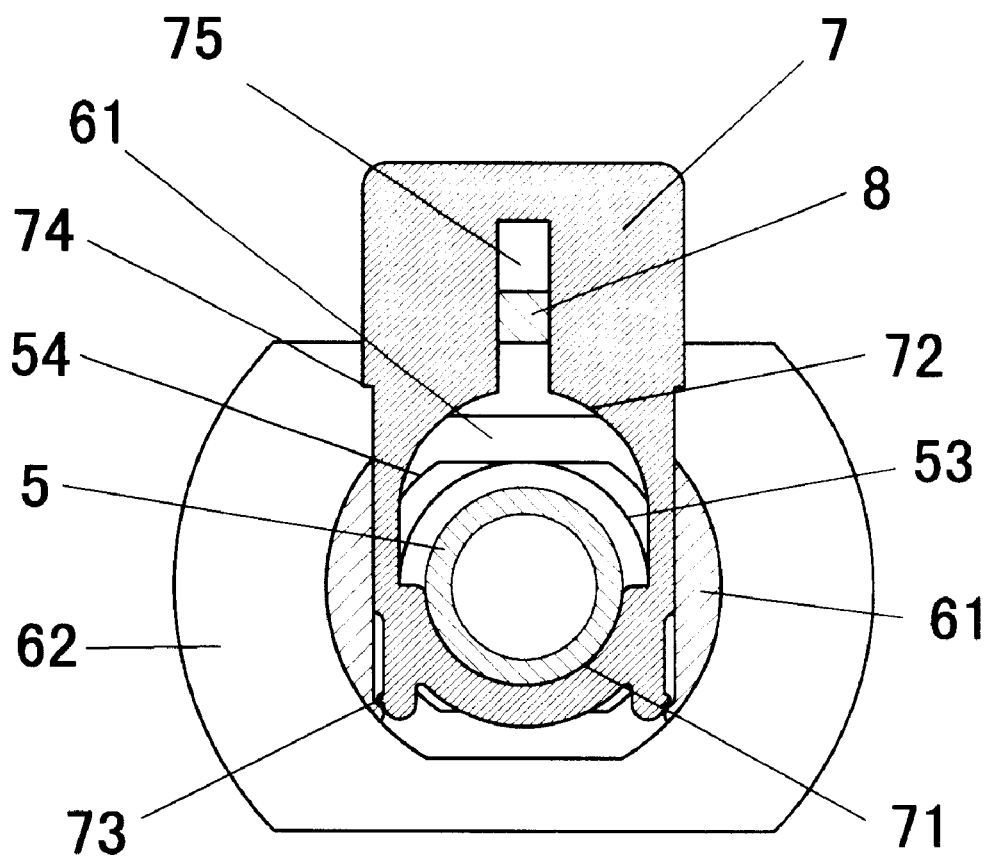
FIG. 8 is a cross sectional view of the indwelling needle assembly shown in FIG. 1 taken along the line B—B.

Referring now to FIG. 6, the inner needle hub 5 will be described in detail. The inner needle hub 5 has a hollow tubular body, and comprises three portions each having a different outer diameter; a distal end portion 52, an intermediate portion 53, and a proximal end portion 54. The outer diameter of the distal end portion 52 is smaller than the inner diameter of the proximal end portion of the outer needle hub 3, the outer diameter of the intermediate portion 53 is larger than the inner diameter of the proximal end portion of the outer needle hub 3 and slightly smaller than the inner diameter of a jutting portion 613 provided on the inner tube 61 (described below), and the outer diameter of the proximal end portion 54 is larger than the inner diameter of the jutting portion 613 and slightly smaller than the inner diameter of the inner tube 61. The proximal end portion 54 has a configuration in cross section such that an upper part and a lower part of a circle are cut away (as shown in FIG. 7(a) and FIG. 8).

A shoulder portion 51 is formed by the difference of the outer diameters of the distal end portion 52 and the intermediate portion 53. The shoulder portion serves in such a manner that when the outer needle 2 and the inner needle 4 are pierced into the patient, the inner needle 4 is positioned in the lumen of the outer needle 2 such that the proximal end portion of the outer needle hub 3 contacts the shoulder portion 51 of the inner needle hub 5, so that the inner needle 4 is used in a state of being positioned in the outer needle 2. At this time, the blade edge 41 of the inner needle 4 projects from the distal end of the outer needle 2 as described above.

As a material for the inner needle hub 5, a transparent or translucent hard material such as polycarbonate, acrylonitrile-butadiene-styrene copolymer, polystyrene, polyethylene, polypropylene, or the like is preferably employed. Such materials allow the user to verify a backflow of blood when the inner needle 4 is pierced into the patient.

The distal end portion 52 of the inner needle hub 5 has a plurality of ribs 56 formed around the circumference thereof. The ribs 56 join the inner periphery of the proximal end portion of the outer needle hub 3, so that the inner needle hub 5 does not move unstably in the outer needle hub 3.

A groove 57 is formed on the outer periphery of the intermediate portion 53 of the inner needle hub 5, and thus the outer diameter of the intermediate portion 53 is correspondingly reduced. The groove 57 is used to fit an inner needle hub locking means 7 (described below) and to lock the inner needle hub 5 while the inner needle 4 is projected from the distal end of the outer needle 2, in other words, in a state before the inner needle 4 is stored in the needle guard 6.

A jutting portion 55 is formed on the inner periphery of the proximal end portion 54 of the inner needle hub 5. The jutting portion 55 serves to fix a connector 8 (described below) when a connecting portion 81 of the connector 8 is inserted into the inner needle hub 5 by fitting in a groove 83 formed on the connector 8.

The lumen of the inner needle hub 5 is in communication with the outside of the indwelling needle assembly 1 only via a filter 9 provided in the intermediate portion 53 and the proximal end portion 54 as shown in FIG. 1. The filter 9 is formed of a material which allows air to pass through but not blood. More specifically, a sintered filter formed of a synthetic resin such as polypropylene, polystyrene, polymethylmethacrylate or the like or a nonwoven fabric or the like is preferably employed. Therefore, when the inner needle 4 and the outer needle 2 are pierced into the blood vessel of a patient, air in the inner needle 4 and the inner needle hub 5 is discharged through the filter 9 to the outside of the indwelling needle assembly 1 and thus a backflow of the blood can be verified. However, blood flowing back into the inner needle 4 and the inner needle hub 5 will not leak to the outside owing to the filter 9.

The needle guard 6 has a double-tube structure comprising an inner tube 61 and an outer tube 62. The outer diameter of the inner tube 61 is slightly smaller than the inner diameter of the outer tube 62, so that the inner tube 61 is able to slide with respect to the outer tube 62.

Figure 7B:
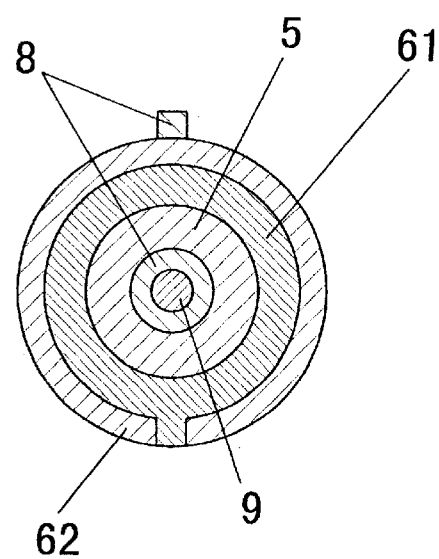

The inner tube 61 and the outer tube 62 preferably have configurations in cross section such that a part of a circle is cut away as shown in FIG. 7(a) or they may be fitted together at a projection formed on the inner tube 61 with a depression formed on the outer tube 62 so as not to rotate with respect to each other about the co-axis as shown in FIG. 7 (b). Alternatively, the inner needle hub 5 has the same configuration as the inner tube 61 and the outer tube 62 as shown in FIG. 7(a) so as not to rotate with respect to each other.

As a material for the inner tube 61 and the outer tube 62, a transparent or translucent hard material such as polycarbonate, acrylonitrile-butadiene-styrene copolymer, polystyrene, polyethylene, polypropylene, or the like is preferably employed.

The inner tube 61 includes a hole 611 in the vicinity of the distal end portion formed through in the vertical direction as shown in FIG. 1. The hole 611 is used for insertion of an inner needle hub locking means 7 (described below) therethrough to lock the inner needle hub 5 in the inner tube 61 in a state before the inner needle 4 is stored in the needle guard 6.

Figure 2:
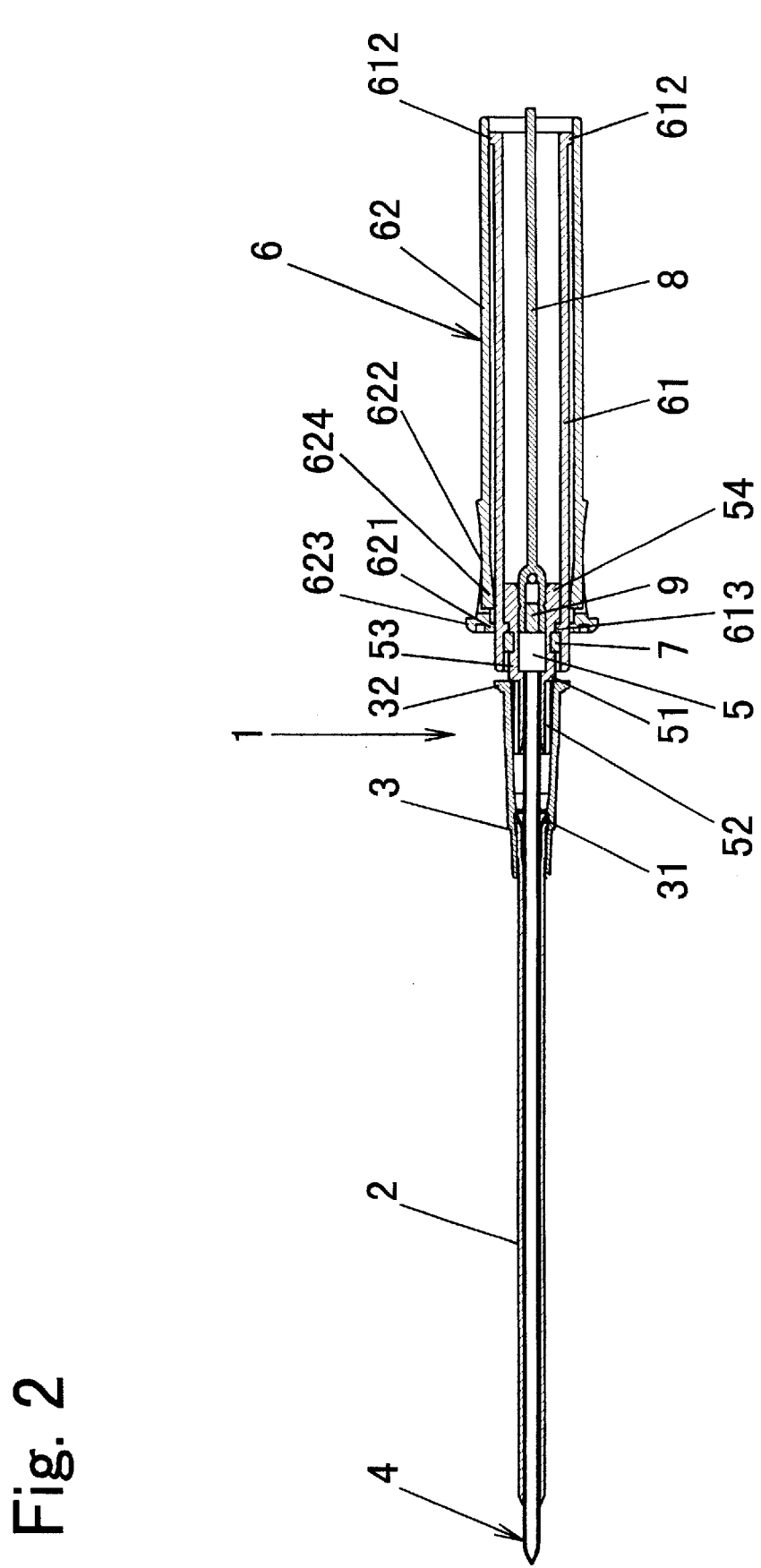
FIG. 2 is a cross sectional view of the indwelling needle assembly shown in FIG. 1 as seen from the top.

The inner tube 61 is provided with jutting portion 612 projecting outwardly on its proximal end portion and with jutting portion 613 projecting inwardly on its distal end portion as shown in FIG. 2. The jutting portion 612 engages an inner engaging projection 621 formed on the distal end portion of the outer tube 62 and serves as a part of an engaging means for fixing the needle guard 6 in a state that the outer tube 62 is slid toward the proximal end of the inner tube 61 until the needle guard 6 is extended to a maximum length. The jutting portion 613 is formed in such a manner that the inner diameter thereof is smaller than the outer diameter of the proximal end portion 54 of the inner needle hub 5 to be inserted in the inner tube 61, so that the inner needle hub 5 is prevented from being detached from the distal side of the inner tube 61.

As shown in FIG. 2, the outer tube 62 is provided on the distal end thereof with an engaging projection 621 as a part of the engaging means described above. The engaging projection 621 is formed to project inwardly until it comes into contact with the inner tube 61, and the outer tube 62 is slid toward the proximal end of the inner tube 61 until the engaging projection 621 engages the jutting portion 612 of the inner tube 61.

In order to handle the indwelling needle assembly 1 easily, there may be provided on the distal end portion of the outer tube 62 a grip part 622 having a curved portion to which the finger tip of the user touches inwardly, or with a stopper 623 or the like so as to prevent the user's finger from slipping. The stopper 623 may be configured to engage a protection cap (not shown) for protecting the outer needle 2 and the inner needle 4 of the indwelling needle assembly 1 before use.

Figure 3:
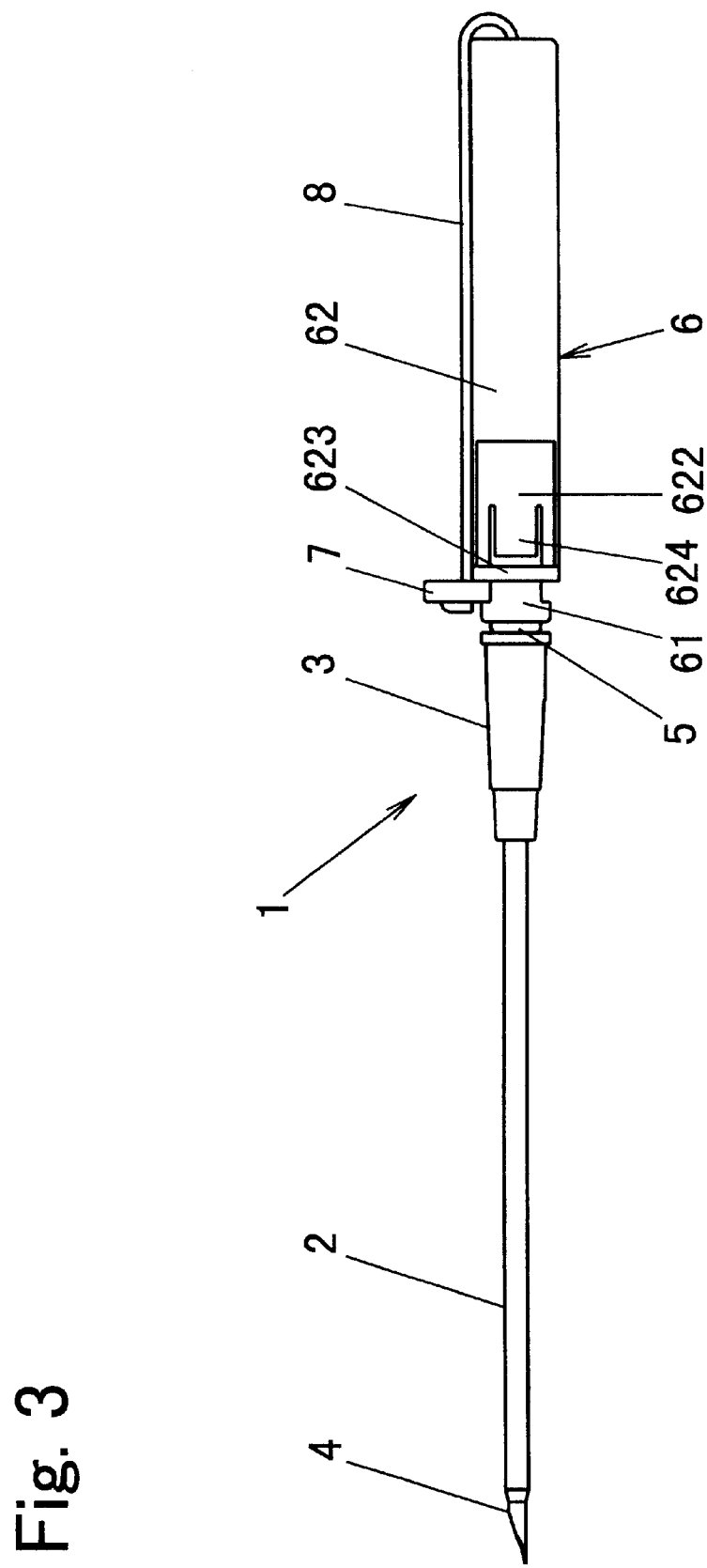
FIG. 3 is a side view of the indwelling needle assembly shown in FIG. 1.
Figure 5:
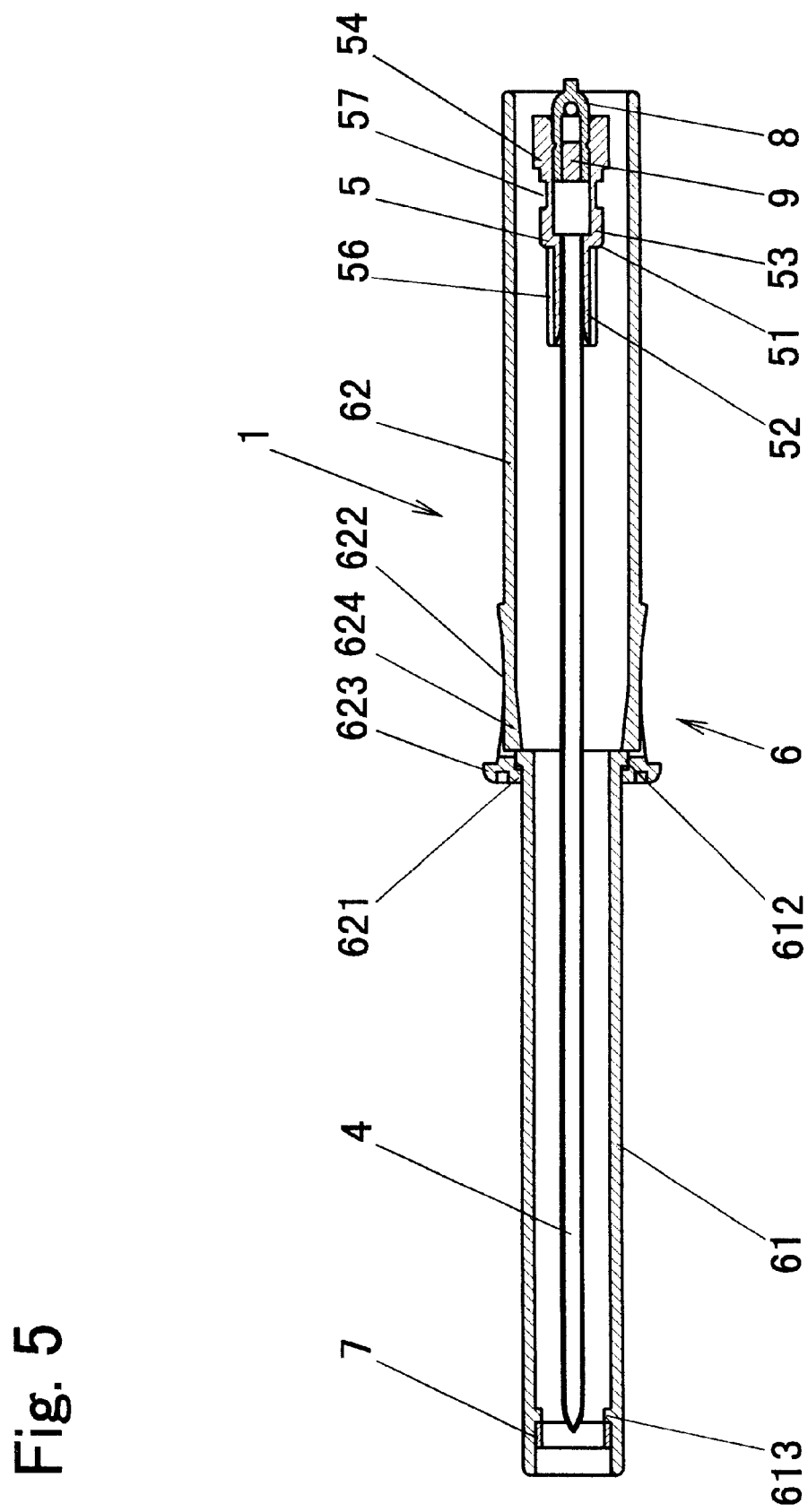
FIG. 5 is a cross sectional view of the indwelling needle assembly shown in FIG. 4 as seen from the top.

In addition, the outer tube 62 maybe provided with an engaging plate 624 projecting inwardly until a part of the outer tube 62 comes into contact with the inner tube 61 and having a configuration shown in FIG. 3 for example. When the outer tube 62 is slid toward the proximal end of the inner tube 61, the jutting portion 612 of the inner tube 61 will slide toward the distal end of the outer tube 62 and will urge the engaging plate 624 outwardly, and will subsequently engage between the engaging projection 621 and the engaging plate 624 as shown in FIG. 5. At this time, the engaging plate 624 is returned to the state before being urged outwardly to prevent the jutting portion 612 from returning toward the proximal end of the outer tube 62.

By providing the engaging plate 624 on the grip part 622 and forming the plate in such a thickness as to project upwardly from the grip part 622 when being urged outwardly by the jutting portion 612, the user can feel when the jutting portion 612 of the inner tube 61 is engaged between the engaging projection 621 and the engaging plate 624 of the outer tube 62 since the urged engaging plate 624 is in contact with the user's fingertip. Consequently, the needle guard 6 is stably fixed and thus there is no possibility that the outer tube 62 can slide toward the distal end of the inner tube 61 and that the blade edge 41 of the inner needle 4 will project again from the distal end portion of the needle guard 6 due to insufficient fixation.

The inner needle hub locking means 7 to be inserted into the hole 611 formed in the inner tube 61 has hole sections 71 and 72 in the lower portion as shown in FIG. 8. The hole section 71 has a semicircular shape having the upper half cut away and having a diameter slightly larger than the outer diameter of the groove 57 of the inner needle hub 5 and smaller than the outer diameter of the intermediate portion 53 (other than the diameter of the groove 57) of the inner needle hub 5. The hole section 72 has a shape of a combination of a semicircle having the lower half cut away and a rectangle, and having a size through which the intermediate portion 53 of the inner needle hub 5 can pass.

In the indwelling needle assembly 1 before use as shown in FIG. 1, the inner needle hub locking means 7 is inserted into the hole 611 formed in the inner tube 61, and the inner needle hub 5 is secured in the distal end of the inner tube 61 by engagement of the hole section 71 with the groove 57 of the inner needle hub 5. When the indwelling needle assembly 1 is pierced into the patient's body and the inner needle 4 is pulled out but the outer needle 2 is retained in the patient's body, the inner needle hub locking means 7 is pushed downward with a finger. With this action, the hole section 71 that has been engaged with the inner needle hub 5 is displaced downward and the intermediate portion 53 of the inner needle hub 5 is positioned in the hole section 72, and then the inner needle hub 5 can move in the inner tube 61 toward the proximal end. Therefore, the inner needle 4 can be slid together with the inner needle hub 5 in the inner tube 61 toward the proximal end and stored in the needle guard 6.

By inserting the inner needle hub locking means 7 into the hole 611 of the inner tube 61, the outer tube 62 is locked by the inner needle hub locking means 7 so as not to slide toward the distal end of the inner tube 61.

On the other hand, the inner needle hub locking means 7 may be provided with an engaging projection 73 or the like for engaging the rim of the hole 611 to ensure insertion to a position to lock the inner needle hub 5 in the distal end of the inner tube 61 before use of the indwelling needle assembly 1. It is also possible to provide an engaging projection 74 or the like so that the inner needle hub locking means 7 can be pressed down to a position where the inner needle hub 5 can move in the inner tube 61 toward the proximal end when storing the inner needle 4 and the inner needle hub 5 in the needle guard 6.

Above the hole section 72 formed in the inner needle hub locking means 7, there may be provided a groove 75 having an inner width slightly larger than the outer width of a connector 8 (described below) but too small for the engagement hook 82 to pass through so that an engagement hook 82 of the connector 8 can be engaged with the groove 75.

As a material for the inner needle hub locking means 7, a hard material such as polyacetal, polycarbonate, acrylonitrile-butadiene-styrene copolymer, polystyrene, polyethylene, polypropylene or the like is preferably employed.

The present invention is characterized in that the needle guard 6 of the indwelling needle assembly 1 is provided with the connector 8. The connector 8 is a string made of soft thermoplastic resin. Preferably the connector 8 does not change in length largely when it is pulled along its length, and more specifically, is preferably made of polyethylene, polypropylene or the like.

Figure 4:
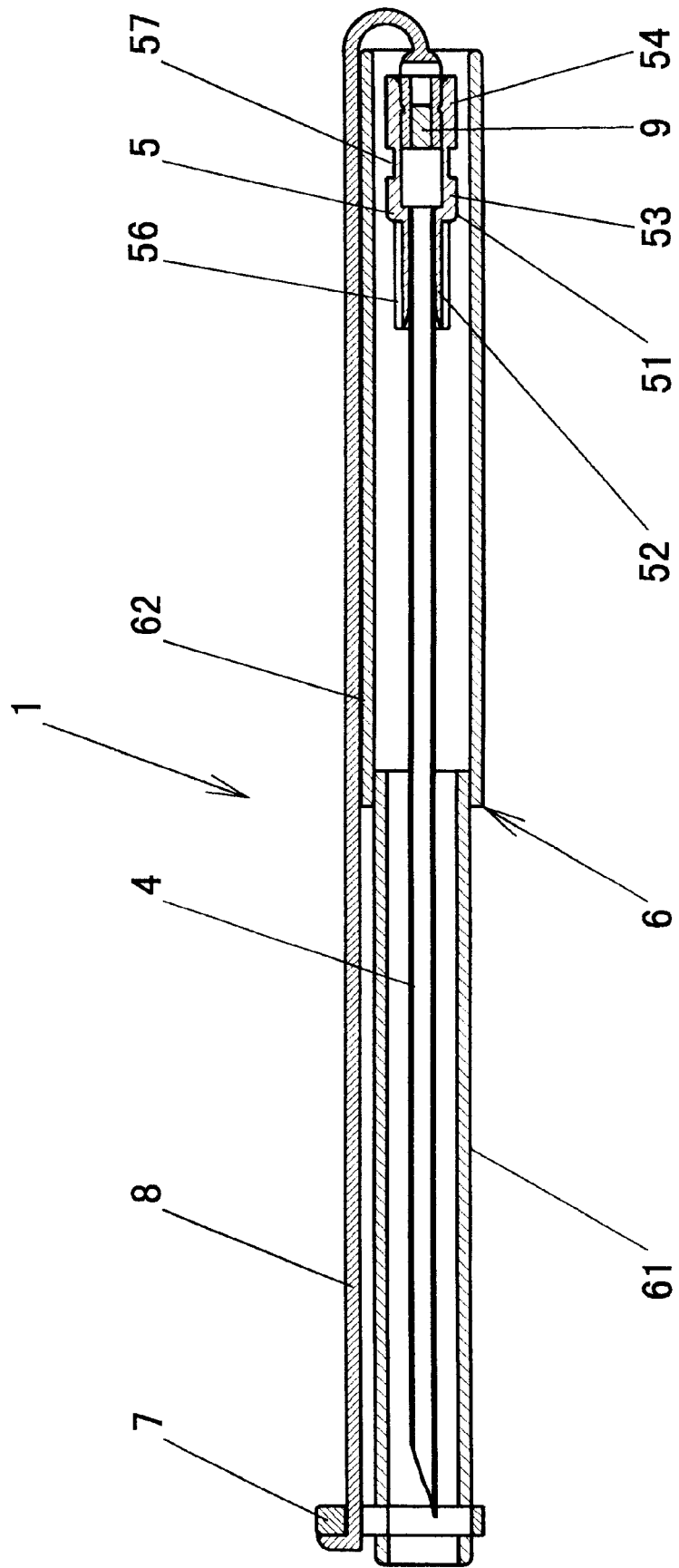
FIG. 4 is a cross sectional view of the indwelling needle assembly according to an embodiment of the present invention showing a state after the inner needle is protected as seen from the side.
Figure 9:
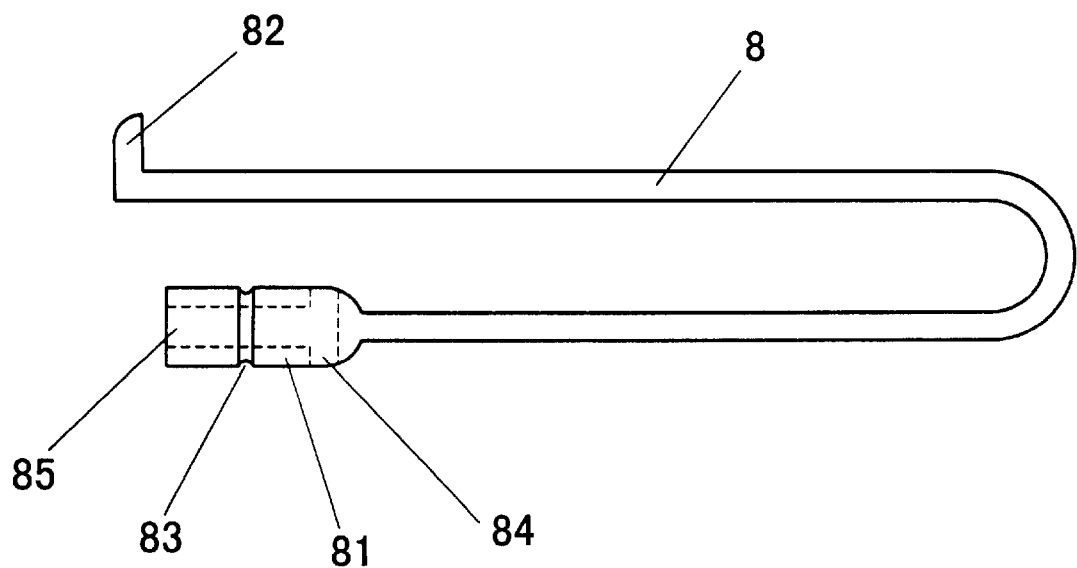
FIG. 9 is a side view of the connector of the indwelling needle assembly shown in FIG. 1.

The connector 8 serves to connect the inner needle hub 5 and the inner tube 61 via the proximal end of the needle guard 6. The connecting method may be any of a rib fit, pressure adhesion, heat welding or the like, and is not specially limited unless it is easily detached when using the indwelling needle assembly 1. Referring now to FIG. 1, FIG. 4 and FIG. 9, an example will be described in detail.

The connector 8 shown in FIG. 9 includes a connecting portion 81 to be connected with the inner needle hub 5. The connecting portion 81 is in a shape of a cylinder having a lumen 85, and the outer diameter of the connecting portion 81 is slightly smaller than the inner diameter of the proximal end portion 54 of the inner needle hub 5 so that the connecting portion 81 can be inserted into the inner needle hub 5. The inner diameter of the connecting portion 81 is formed in a size through which the filter 9 can be inserted therein.

The outer periphery of the connecting portion 81 of the connector 8 is provided with a groove 83 for fitting the jutting portion 55 (FIG. 6) provided in the inner needle hub 5 described above. The connector 8 is connected to the inner needle hub 5 in such a manner that a filter 9 is first inserted in the lumen 85, then the connector 8 is inserted into the inner needle hub 5 in the state as-is, and then the jutting portion 55 in the inner needle hub 5 engages the groove 83. Since the connector 8 is made of a soft thermoplastic resin and the filter 9 has resiliency, the outer diameter of the connecting portion 81 is reduced by the jutting portion 55 and the connector 8 is inserted into the inner needle hub 5. After insertion, blood flowing back into the inner needle hub 5 is blocked by the filter 9. Since the filter 9 swells with the blood, the outer diameter of the connecting portion 81 resists being reduced due to the jutting portion 55 in the inner needle hub 5 in contrast to the case of insertion and the connector 8 cannot be detached from the inner needle hub 5 even when an external force is applied to the connector 8 by a sliding movement of the inner tube 61 toward the distal end of the outer tube 62. In addition, a hole 84 is provided on the proximal side in the connecting portion 81 of the connector 8 in which the filter 9 is inserted. The hole 84 prevents the lumen of the inner needle hub 5 from being hermetically closed when the connector 8 is inserted into the inner needle hub 5. The hole 84 may be formed either in a vertical direction as shown in FIG. 9 or in a horizontal direction (not shown).

On the other hand, an engaging hook 82 is provided on the opposite end of the connecting portion 81 of the connector 8. The connector 8 and the inner tube 61 can be connected indirectly by fitting the connector 8 in the groove 75 (FIG. 8) formed in the inner needle hub locking means 7 and engaging the engaging hook 82 with the distal end of the inner needle hub engaging means 7.

As a next stage, in the indwelling needle assembly 1 of the present invention, the connector 8 is connected, for example, to an intermediate portion 53 and a proximal end portion 54 of the inner needle hub 5 at one end, and arranged in the proximal end of the inner needle hub 5 through the inside of the needle guard 6. The connector 8 is also arranged outside of the needle guard 6 via the proximal end of the needle guard 6, and engaged with the inner needle hub locking means 7 inserted into the distal end of the inner tube 61 via the engaging hook 82, and thus indirectly connected to the inner tube 61 as shown in FIG. 1. After use of the indwelling needle assembly 1, the inner needle hub locking means 7 inserted into the hole 611 of the inner tube 61 is pressed down and the outer tube 62 is slid toward the proximal end of the inner tube 61, so that the inner needle 4 and the inner needle hub 5 are pulled by the connector 8 and stored in the needle guard 6. At this time, since the connector 8 is always arranged on the proximal side of the outer tube 62, the distance of movement of the outer tube 62 toward the proximal end of the inner tube 61 is about half the distance of movement of the inner needle hub 5 in the needle guard 6 toward the proximal end. Therefore, in order to bring the indwelling needle assembly 1 into the state shown in FIG. 4, the outer tube 62 is moved toward the proximal end of the inner tube 61 by a distance corresponding to approximately half the length between the distal end of the inner needle 4 and the inner needle hub 5, and thus medical personnel can protect the inner needle 4 easily using one hand even when the inner needle 4 is long or even when it is used by medical personnel whose hands are small.

The length of the connector 8 of the present invention is preferably such that it does not prevent the needle guard 6 from being extended to its maximum length, as well as does not sag at the proximal end of the outer tube 62.

Figure 10:
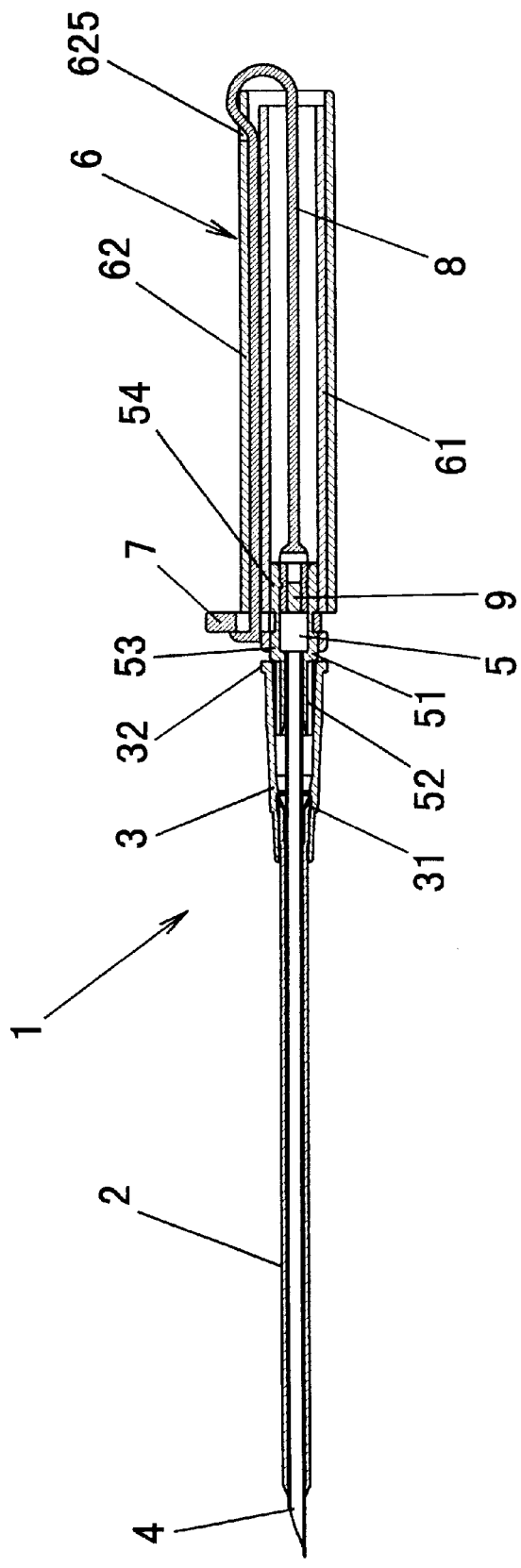
FIG. 10 is a cross sectional view of the indwelling needle assembly according to another embodiment of the present invention showing a state before the inner needle is protected as seen from the side.
Figure 11:
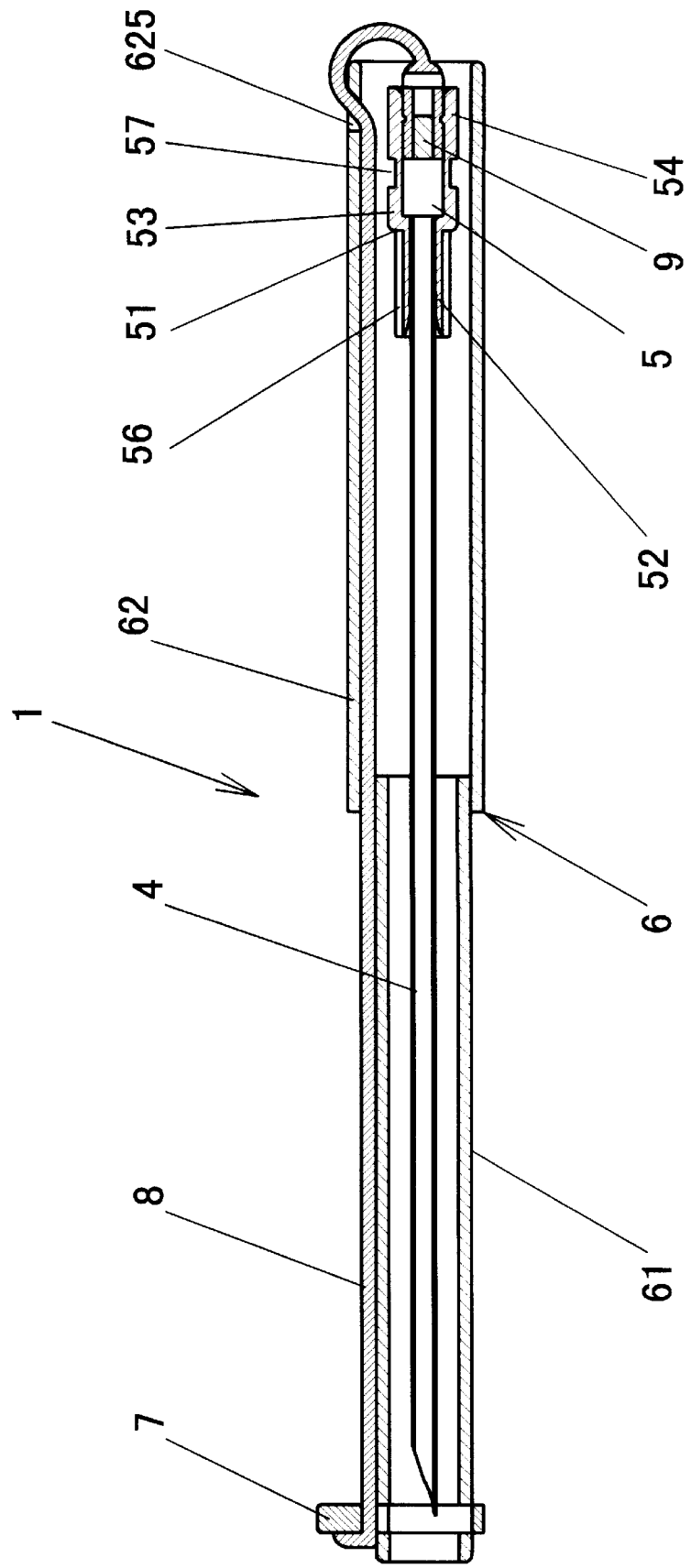
FIG. 11 is a cross sectional view of the indwelling needle assembly according to another embodiment of the present invention in a state after the inner needle is protected as seen from the side.

In FIG. 10 and FIG. 11, another embodiment of the indwelling needle assembly 1 according to the present invention is illustrated. According to FIG. 10 and FIG. 11, the connector 8 is connected at one end to the intermediate portion 53 and the proximal end portion 54 of the inner needle hub 5, arranged in the proximal end of the inner needle hub 5 through the inside of the needle guard 6. The connector 8 is then arranged outside of the needle guard 6 via the proximal end of the needle guard 6, passed through a hole 625 formed in the outer tube 62 of the needle guard 6 and arranged in the clearance between the outer tube 62 and the inner tube 61. Further, it is engaged with the inner needle hub locking means 7 inserted into the distal end of the inner tube 61 by the engaging hook 82, and thus indirectly connected to the inner tube 61.

With the indwelling needle assembly 1 shown in FIG. 10 and FIG. 11, the same effect as the indwelling needle assembly 1 shown in FIG. 1 to FIG. 5 can be expected. Though the indwelling needle assembly 1 requires another step to arrange the connector 8 in the clearance between the inner tube 61 and the outer tube 62 in comparison with the indwelling needle assembly 1 shown in FIGS. 1 to 5, it eliminates the possibility that the fingers of the user will become entangled with the connector 8 arranged outside the outer tube 62.

In the indwelling needle assembly 1, the configuration of the clearance between the inner tube 61 and the outer tube 62 in which the connector 8 is arranged is not limited as far as it does not interfere with the operation of the indwelling needle assembly 1. However, it is more preferable to provide a groove for arranging the connector 8 extending longitudinally along the inner periphery of the outer tube 62 or the same groove on the outer periphery of the inner tube 61.

The configuration of the indwelling needle assembly 1 of the present invention is not limited to the configurations shown in FIG. 1 to FIG. 11, but may be any configuration as far as the connector 8 connects the inner needle hub 5 and the inner tube 61 via the proximal end of the outer tube 62. The connector 8 does not necessarily have to be disposed on the proximal side of the outer tube 62, but it may be disposed at different positions within a range in which the effect of the present invention is not impaired. For example, it may engage the proximal end of the outer tube 62 through a hole formed at the proximal end of the outer tube 62. Therefore the present invention includes various configurations of the indwelling needle assembly 1 according to the arrangement of the connector 8.

Figure 12A:
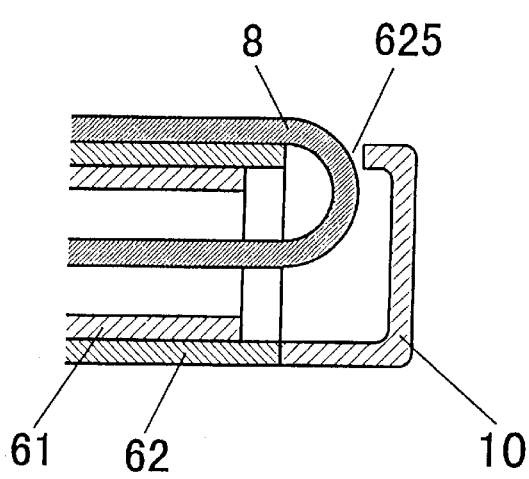
FIG. 12 is a cross sectional view of the indwelling needle assembly of the present invention showing embodiments of the proximal end portion of the needle guard.
Figure 12B:
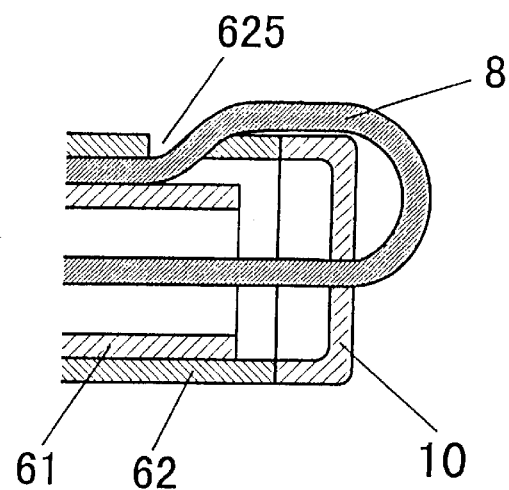

The indwelling needle assembly 1 of the present invention may be provided with a cap 10 at the proximal end of the needle guard 6 as shown in FIGS. 12(a) and (b) for preventing blood attached to the inner needle 4 and the inner needle hub 5 stored in the needle guard 6 from leakage, or for preventing the user of the indwelling needle assembly 1 from coming into contact with blood adhered to the inner needle 4 and the inner needle hub 5. The configuration of the cap 10 may be formed in a preferred configuration depending on the arrangement of the connector 8. For example, in case of the indwelling needle assembly 1 shown in FIG. 1, the cap 10 having a configuration shown in FIG. 12(a) is preferably used, and in case of the indwelling needle assembly 1 shown in FIG. 10, the cap 10 having a configuration shown in FIG. 12(b) is preferably used.

Effect of the Invention

In the indwelling needle assembly of the present invention, a connector for connecting the inner needle hub and the inner tube via the proximal end of the outer tube can reduce the distance of movement of the needle guard to about half that in a conventional indwelling needle assembly, so that the inner needle can be protected using one hand even when it is used by medical personnel having small hands. In addition, a long indwelling needle to be retained in a femoral vein in an inguinal region when emergently dialyzing can not be used in a conventional indwelling needle assembly, but can be used in the indwelling needle assembly of the present invention.

Even when the user inadvertently presses the inner needle hub locking means down and releases the inner needle hub, it can be returned to the original position, and then the indwelling needle assembly will not be put out of use.

What is claimed is:

1. An indwelling needle assembly comprising an outer needle hub having a distal end portion and a proximal end portion; an outer needle to be pierced into tissue of a living body and retained in the body fixed to the distal end portion of said outer needle hub; an inner needle hub fitted in the proximal end of the outer needle hub and having a distal end portion, an intermediate portion and a proximal end portion; an inner needle slidably inserted in a lumen of said outer needle, said inner needle having a sharp blade edge at a distal end portion thereof and being fixed to the distal end portion of said inner needle hub; and a needle guard detachably connected to said inner needle hub for accommodating said inner needle and said inner needle hub after use; said needle guard having a distal end and a proximal end and comprising a double-tube structure of an inner tube and an outer tube slidably positioned over said inner tube, each of said inner tube and said outer tube having a distal end and a proximal end, a flexible elongated connector having a first end connected to said inner needle hub, a second end connected to the distal end of the inner tube and an intermediate portion connecting said first end of the connector and said second end of the connector via the proximal end of said needle guard, wherein the whole length of said needle guard can be extended by sliding said outer tube toward the proximal end of said inner tube such that as a whole length of said needle guard is extended, said inner needle hub and inner needle is slid within said needle guard toward the proximal end of said needle guard by said connector.

2. The indwelling needle assembly claimed in claim 1, wherein said connector extends from the proximal end portion of the inner needle hub along the inside of the needle guard and the proximal end portion of the needle guard to the outside of the needle guard, and connects the proximal end portion of the inner needle hub and the distal end of the inner tube.

3. The indwelling needle assembly claimed in claim 1, wherein said connector extends from the proximal end portion of the inner needle hub along the inside of the needle guard and the proximal end portion of the needle guard through the inside of a hole formed on the proximal end portion of the outer tube of the needle guard and between a clearance between the outer tube and the inner tube of the needle guard, and connects the proximal end portion of the inner needle hub and the distal end of the inner tube.

4. The indwelling needle assembly claimed in claim 3, wherein the clearance between the outer tube and the inner tube of said needle guard is a groove formed within the outer tube along the length of the outer tube.

5. The indwelling needle assembly claimed in claim 1, wherein an inner needle hub locking means for maintaining the inner needle hub in a position where said inner needle is projected from the distal end of the outer needle is provided on the distal end portion of said inner tube, and engaging means for fixing said inner tube and said outer tube in a relative position when said needle guard is extended are provided on the inner tube and the outer tube so that said inner needle can be stored in the needle guard.

6. The indwelling needle assembly claimed in claim 5, wherein said engaging means comprises a jutting portion provided on the proximal end portion of the inner tube and projecting outwardly; an engaging projection provided on the distal end portion of the outer tube and projecting inwardly; and an engaging plate provided on the distal end portion of the outer tube on the proximal side of said engaging projection and projecting inwardly to contact the inner tube, said engaging plate being spaced apart from said engaging projection a distance for engaging the jutting portion of said inner tube between said engaging plate and said engaging projection and having a thickness so as to project from the outer tube when urged outwardly by the jutting portion of said inner tube as the needle guard is extended.

7. An indwelling needle assembly claimed in claim 1, characterized in that said connector is formed of a string made thermoplastic resin.

* * * * *